United States Patent [19]
Pike

[11] Patent Number: 5,968,518
[45] Date of Patent: Oct. 19, 1999

[54] COMPOSITION AND METHOD FOR TREATING PREMENSTRUAL SYNDROME

[76] Inventor: Laurie Pike, 10444 NW. 1st Ct., Coral Springs, Fla. 33071

[21] Appl. No.: 09/027,147

[22] Filed: Feb. 20, 1998

[51] Int. Cl.[6] .............................. A61K 35/78; A61K 9/50
[52] U.S. Cl. ...................... 424/195.1; 424/489; 424/498; 514/899
[58] Field of Search ............................ 424/195.1, 489, 424/498; 514/899

[56] References Cited

U.S. PATENT DOCUMENTS 5,569,458 10/1996 Greenberg ........................ 424/195.1
5,707,630 1/1998 Morrow ............................ 424/195.1

*Primary Examiner*—Leon B. Lankford, Jr.
*Assistant Examiner*—Christopher R. Tate
*Attorney, Agent, or Firm*—Cooper & Dunham LLP; Robert D. Katz, Esq.

[57] ABSTRACT

An herbal composition is disclosed comprising as active ingredients chickweed, yarrow, wormwood, motherwort, pennyroyal, and dandelion in a vehicle of olive-oil and beeswax. The composition alleviates cramps, aches and pains, such as those associated with premenstrual syndrome.

6 Claims, No Drawings

COMPOSITION AND METHOD FOR TREATING PREMENSTRUAL SYNDROME

FIELD OF THE INVENTION

This invention relates to an herbal composition for treating the symptoms of premenstrual syndrome, including menstrual cramps, aches and pains, and bloating. The invention also relates to a method for treating some of the symptoms associated with premenstrual syndrome, particularly aches, pains, and cramps using herbal compositions.

BACKGROUND OF THE INVENTION

The days preceding the onset of the menstrual period involve hormonal changes which can result in symptoms such as cramping, aches, bloating, and inflammation. These symptoms, commonly referred to as premenstrual syndrome, or PMS, are treated by a variety of means. Simple ones include taking ibuprofen or acetaminophen for aches and pains, and various other substances for bloating or water retention. Many over the counter remedies are available for these common symptoms, and in many cases may provide temporary or limited relief.

Other approaches involve attempts to correct apparent hormonal imbalances which may be present prior to menstruation. For example, according to U.S. Pat. No. 5,707,630 (Morrow), the symptoms of PMS and menopause can be treated with an herbal composition including red raspberry, bayberry, blue cohosh, capsicum, cascara sagrada, damiana, ginger, avalcrian administered orally in tablet form using a binding agent. The patentee claims that the foregoing herbal compound alleviates the symptoms associated with PMS and menopause.

U.S. Pat. No. 5,565,199 (Page) states that phytohormone, such as phytoestrogens and phytoprogesterone, from herbaceous plants provide means for balancing estrogen and progesterone levels in organisms without producing undesirable physiological side effects. According to the patent, herbaceous plants contain many types of regulating substances, some of which are known as phytohormone. These plants assertedly provide a source of natural base steroidal hormones which may provide estrogenic or progesterone hormone activity to enhance or supplement the hormonal levels in biological organisms.

The foregoing remedies do not provide complete or even satisfactory relief of cramps, bloating, and inflammation in many patients, and involve ingestion of substances which may introduce other difficulties or side effects. Therefore, there continues to be a need for a safe and effective composition to treat some of the aches and cramps associated with premenstrual syndrome or other ailments.

SUMMARY OF THE INVENTION

The invention provides an herbal composition comprising chickweed, yarrow, wormwood, motherwort, pennyroyal, and dandelion as active ingredients. The invention preferably includes a vehicle comprising olive oil and beeswax, and the vehicle may additionally contain tincture of benzoin or another compatible preservative. Preferably, the active ingredients are present in approximately equal amounts, in a range from about 75 mg to about 150 mg of each herb for every fluid ounce of vehicle. Cayenne may be used to increase absorption.

The invention also provides a method for treating menstrual or other cramps comprising applying an effective amount of a composition comprising chickweed, yarrow, wormwood, motherwort, pennyroyal, and dandelion as active ingredients to an affected area, such as a portion of the abdomen of an affected female. In another embodiment, the invention provides a method for relieving an ache or pain, such as a muscle ache, back ache, stomach ache, head ache, neck ache or similar minor ache or pain, which comprises applying an herbal composition comprising chickweed, yarrow, wormwood, motherwort, pennyroyal, and dandelion, preferably in a vehicle containing olive oil and beeswax, to an affected area of a patient. Optionally, the treatment can include application of heat for about five to ten or more minutes.

Further features and advantages of the invention will become apparent upon review of the following detailed description of the preferred embodiments.

DETAILED DESCRIPTION OF THE PREFERRED EMBODIMENTS

The present invention is directed to an herbal compound and method for treatment which uses such a compound to aid in the relief of symptoms such as cramping, bloating, and inflammation caused by premenstrual syndrome. In one preferred embodiment, the herbal compound of the present invention comprises chickweed, yarrow, wormwood, motherwort, pennyroyal, and dandelion, preferably in a vehicle which contains olive oil and beeswax. The composition, usually in the form of an ointment, is rubbed on an affected area, such as the abdomen of a woman suffering from premenstrual cramps.

The following herbs are included in the preferred embodiments. Following each is a brief description of its activity:

| Herb | Part Used | Vitamins | Actions | Comments |
|---|---|---|---|---|
| Cayenne | Berries | Apsaicine, capacutin, capasaicin, capsanthine, capsico, cobalt, folic acid, pantothenic acid, para-aminobenzoic acid, zinc, vitamins A, $B_1$, $B_2$, $B_3$, $B_6$, and C. | Aids digestion, improves circulation, and stops bleeding from ulcers. Acts as a catalyst for other herbs. Good for the heart, kidneys, lungs, pancreas, spleen, and stomach. Useful for arthritis and rheumatism. Helps to ward off colds, sinus infections, and sore throats. Good for pain when applied topically. Used with lobelia for nerves. | Also called capsicum, hot pepper, red pepper. |

| Herb | Part Used | Vitamins | Actions | Comments |
|---|---|---|---|---|
| Dandelion | Leaves, roots, tops. | Bioflavonoids, biotin, calcium, choline, fats, folic acid, gluten, gum, inositol, inulin, iron, lactupicrine, linolenic acid, magnesium, niacin, pantothenic acid, para-aminobenzoic acid, phosphorus, potash, proteins, resin, sulfur, zinc, vitamins A, $B_1$, $B_2$, $B_6$, $B_{12}$, C, and E. | Cleanses the bloodstream and liver, and increases the production of bile. Used as a diuretic. Also reduces serum cholesterol and uric acid. Improves functioning of the kidneys, pancreas, spleen, and stomach. Useful for abscesses, anemia, boils, breast tumors, cirrhosis of the liver, fluid retention, hepatitis, jaundice, and rheumatism. May aid in the prevention of age spots and breast cancer. | The roasted root can be used as a coffee substitute. |
| Wormwood | Leaves, tops. | Absinthol, acetylene, artemisia ketone, essential oils, flavonoids, lignin, phenolic compounds, pinene, thujone. | Acts as a mild sedative, expels worms, increases stomach acidity, and lowers fever. Useful for vascular disorders, including migraine, and for intestinal parasites. | Often used with black walnut for removal of parasites. Caution: Should not be used during pregnancy, as it can cause spontaneous abortion. Not recommended for long-term use, as it can be habit-forming. |

| Herb | Part Used | Vitamins | Actions | Comments |
|---|---|---|---|---|
| Yarrow | Berries, leaves. | Achilleic acid, achilleine, caledivain, volatile oils, potassium, tannins, vitamin C. | Has healing effects on mucous membranes, reduces inflammation, improves blood clotting, increases perspiration. A good diuretic. Useful for fever, inflammatory disorders, colitis, and viral infections. Helps to alleviate bleeding problem. | Also called soldier's herb. Caution: Interferes with absorption of iron and other minerals. |

Chickweed Reduces inflammation and aids in healing.

Pennyroyal (*Hedeoma pulegioides*)—the leaves of the herb are used in remedies; uses include upset stomach and as a gentle stimulant. It is also believed to be useful for menstrual cramps because it stimulates the uterine muscles.

Motherwort is believed to strengthen the nervous system, and is asserted to be a tonic for the whole body; it seems to help those who are prone to headaches and helps relieve menstrual discomfort.

The following examples are illustrative of the practice of the invention and are not meant to be limiting.

EXAMPLE I

The following amounts of each herb were mixed in the olive oil-beeswax vehicle, with tincture of benzoin added as a preservative. All herbs were produced by Frontier Bulk Herbs and Spices, Norway, Iowa.

chickweed—1 oz.

yarrow—1 oz.

wormwood—1 oz.

motherwort—1 oz.

pennyroyal—1 oz.

dandelion—1 oz.

2 cups olive oil, 3 oz.-beeswax, 1 tsp. Tincture of benzoin.

Yield: 12 2 oz. jars.

EXAMPLE II

A 45 year old female started menstruation at age 13 and experienced minor cramping and light bleeding until age 30. At age 30, she had her tubes tied and after that came heavier periods and moderate to severe cramping for the first two days of her cycle.

Female rubbed ointment (sample from example I) for the first time on her lower abdomen when she experienced her first sign of cramps. Cramps went away in 30 minutes. The second day cramps felt worse from first day, she rubbed ointment on abdomen and applied heat. Relief started to take place in 15 to 20 minutes. Cramps were gone after second treatment. Her period lasted a few more days cramp free. Same female used ointment for cramps in lower back with heat, and after 15 minutes, cramps lessened. She also experienced right hip pain, unrelated to menstruation, rubbed ointment on right hip and used with heat and that pain went away also.

EXAMPLE III

A woman who felt bad cramps on the first day of her period at 8:00 a.m applied the composition (ointment) to her abdomen. Relief felt in 20–30 minutes. At 3 p.m cramps returned. At 4:30 p.m., she applied more of composition. Relief occurred in 20 minutes. When cramps recurred at 8:30 p.m., she applied more. Second day cramps were severe. She used ointment in a.m. once and in p.m once. Cramps disappeared. On the third day she used ointment in a.m. to prevent cramps and it worked. Period lasted only three days.

EXAMPLE IV

| | |
|---|---|
| 25 mg. | Cayenne |
| 105 mg. | Chickweed |
| 105 mg | Yarrow |
| 105 mg | Wormwood |
| 105 mg | Dandelion |
| 105 mg | Motherwort |

| | |
|---|---|
| -continued | |
| 105 mg | Pennyroyal |
| 105 mg | Tincture of benzoin |

The above ingredients were mixed into vehicle of 0.17 fluid ounce beeswax and 0.66 fluid ounce olive oil. One percent vanilla added as fragrance.

I claim:

1. A topical herbal composition for treating menstrual cramps comprising the approximately equal amounts by weight of the active parts of the following herbs:

chickweed, yarrow, wormwood, motherwort, pennyroyal, and dandelion.

2. The herbal composition in accordance with claim 1 additionally comprising cayenne.

3. The herbal composition in accordance with claim 2 additionally comprising a vehicle comprising olive oil and beeswax.

4. The herbal composition in accordance with claim 3 wherein the vehicle additionally contains tincture of benzoin as a preservative.

5. A method for treating menstrual cramps comprising applying an effective amount of the herbal composition in accordance with any one of claim 1–4 to an affected area of the abdomen.

6. The method in accordance with claim 5 additionally comprising applying heat to the affected part of the abdomen for about five to ten minutes.

* * * * *